US008670824B2

(12) United States Patent
Anderson et al.

(10) Patent No.: US 8,670,824 B2
(45) Date of Patent: Mar. 11, 2014

(54) SINGLE-PASS LEFT-SIDED DDD PACING LEAD

(75) Inventors: Kenneth M. Anderson, Bloomington, MN (US); John L. Sommer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/568,771

(22) Filed: Aug. 7, 2012

(65) Prior Publication Data

US 2014/0046389 A1 Feb. 13, 2014

(51) Int. Cl.
*A61N 1/00* (2006.01)

(52) U.S. Cl.
USPC .............................................. 607/4

(58) Field of Classification Search
USPC .................................. 607/4, 9, 126
See application file for complete search history.

(56) References Cited

U.S. PATENT DOCUMENTS

| | | | |
|---|---|---|---|
| 5,117,824 A | 6/1992 | Keimel et al. | |
| 5,265,601 A | 11/1993 | Mehra | |
| 5,466,254 A | 11/1995 | Helland | |
| 5,545,204 A | 8/1996 | Cammilli et al. | |
| 5,755,761 A | 5/1998 | Obino | |
| 5,800,465 A * | 9/1998 | Thompson et al. | 607/9 |
| 5,899,929 A | 5/1999 | Thompson et al. | |
| 5,964,795 A | 10/1999 | McVenes et al. | |
| 6,055,457 A | 4/2000 | Bonner | |
| 6,070,104 A | 5/2000 | Hine et al. | |
| 6,083,247 A | 7/2000 | Rutten et al. | |
| 6,096,064 A * | 8/2000 | Routh | 607/9 |
| 6,201,994 B1 | 3/2001 | Warman et al. | |
| 6,363,288 B1 | 3/2002 | Bush et al. | |
| 6,490,489 B2 | 12/2002 | Bornzin et al. | |
| 6,584,362 B1 | 6/2003 | Scheiner et al. | |
| 6,721,598 B1 | 4/2004 | Helland et al. | |
| 6,745,081 B1 | 6/2004 | Helland et al. | |
| 6,760,619 B1 | 7/2004 | Helland et al. | |
| 6,909,920 B2 | 6/2005 | Lokhoff et al. | |
| 6,988,007 B1 | 1/2006 | Morgan et al. | |
| 7,010,358 B1 | 3/2006 | Kroll et al. | |
| 7,139,614 B2 | 11/2006 | Scheiner et al. | |
| 7,860,580 B2 | 12/2010 | Falk et al. | |
| 2011/0015714 A1 * | 1/2011 | Atkinson et al. | 607/126 |

OTHER PUBLICATIONS

Singh et al., "Left Ventricular Lead Position and Clinical Outcome in the Multicenter Automatic Defibrillator Implantation Trial—Cardiac Resynchronization Therapy (MADIT-CRT) Trial," Circulation, 2011;123:1159-1166.

* cited by examiner

*Primary Examiner* — Robert N Wieland
(74) *Attorney, Agent, or Firm* — Reed A. Duthler (57) ABSTRACT

A single-pass pacing lead capable of sensing and pacing both the atria and the ventricles is described. In some examples, the single-pass pacing lead is connected to a DDD pacemaker. In some examples, the single-pass pacing lead comprises four electrodes. In some examples, the lead includes three electrodes configured to be positioned in or near an atrium, e.g., the right atrium, and one electrode configured to be positioned in or near a ventricle, e.g., the left ventricle, when the lead is implanted. In other examples, the lead includes two electrodes configured to be positioned in each of the atrium and ventricle when the lead is implanted. In some examples, one of the electrodes, which is configured to be positioned proximate the coronary sinus ostium when the lead is implanted, comprises a helical element for fixation of the lead to tissue.

24 Claims, 9 Drawing Sheets

SINGLE-PASS LEFT-SIDED DDD PACING LEAD

TECHNICAL FIELD

The disclosure relates to a single-pass pacing lead capable of pacing in both atrial and ventricular chambers.

BACKGROUND

The activity of a normal, healthy heart involves the synchronized contraction of the atria and ventricles of the heart. Blood is received into the atria, which contract, forcing the blood into the ventricles. Subsequent contraction of the ventricles then causes the blood to be pumped through the body and eventually returned to the atria. The contractions of the chambers of the heart are caused by coordinated electrical activation of portions of the cardiac muscle.

The heartbeat cycle begins with the generation of an electrical impulse by a bundle of fibers located in the sinoatrial node of the heart, near the upper portion of the right atrium at the entrance to the superior vena cava. This impulse spreads across the atria, stimulating the atrial muscles and causing the atrial contraction which forces blood into the ventricles. An atrial contraction is manifested as the so-called "P-wave" in an electrocardiographic signal. The electrical impulse conducted through the atrial muscle is then received at the partition wall immediately beside the valve between the right atrium and right ventricle, at the atrio-ventricular or A-V node. The A-V node introduces a slight delay in the transmission of the electrical impulse to the ventricles. This A-V delay is typically on the order of 100 milliseconds. After the A-V delay, the electrical impulse is conducted to the ventricles, causing the ventricular contraction which is manifested as the "QRS complex" of an electrocardiographic signal. Subsequent repolarization and relaxation of the ventricular muscles occurs at the end of the cardiac cycle, which is manifested as the "T-wave" portion of an electrocardiographic signal.

For patients in which the above-described conduction of electrical impulses through the cardiac muscle is somehow impaired, a pacemaker can provide an artificial electrical stimulus where no natural electrical impulse is present. Thus, for example, a ventricular pacemaker can function to cause ventricular contractions in patients in which the natural electrical cardiac impulse is, for some reason, not transmitted across the A-V node. It is important, however, that any artificial stimulating pulses be delivered at appropriated times, so that proper synchronization of atrial and ventricular action is maintained. In addition, it is known that electrical impulses being delivered to the cardiac muscle during the repolarization phase at the end of the cardiac cycle can cause the onset of tachyarrhythmias. It is therefore important that the pacemaker be prevented from delivering stimulating pulses during the T-wave.

In order to maintain A-V synchrony, and to prevent delivery of pacing pulses at undesirable times, pacemakers are preferably capable of detecting either atrial activity, ventricular activity, or both, as manifested by the P-wave and QRS complex (or more typically the R-wave), respectively, via atrial and ventricular cardiac electrogram signals sensed by the pacemaker.

Pacemakers are generally characterized by which chambers of the heart they are capable of sensing, the chambers to which they deliver pacing stimuli, and their responses, if any, to sensed intrinsic electrical cardiac activity. Some pacemakers deliver pacing stimuli at fixed, regular intervals without regard to naturally occurring cardiac activity. More commonly, however, pacemakers sense electrical cardiac activity in one or both of the chambers of the heart, and inhibit or trigger delivery of pacing stimuli to the heart based on the occurrence and recognition of sensed intrinsic electrical events.

The North American Society of Pacing and Electrophysiology (NASPE) and the British Pacing and Electrophysiology Group (BPEG) have adopted a three-letter code which is used to describe the operative modalities of pacemakers. The first letter of the three letter code designates the chamber or chambers of the heart to which the pacemaker delivers pacing pulses; an "A" in the first position designates atrial pacing, a "V" designates ventricular pacing, and a "D" designates both atrial and ventricular pacing. Similarly, the second letter position designates the chambers of the heart from which the pacemaker senses electrical signals, and this second letter may be either an "A" (atrial sensing), a "V" (ventricular sensing), a "D" (atrial and ventricular sensing), or an "O" (no sensing). The third letter position designates the pacemaker's responses to sensed electrical signals. The pacemaker's response may either be to trigger the delivery of pacing pulses based upon sensed electrical cardiac signals (designated by a "T" in the third position), to inhibit the delivery of pacing pulses based upon sensed electrical cardiac signals (designated by an "I" in the third position), or both trigger and inhibit based upon sensed electrical cardiac signals (designated by a "D"). An "O" in the third position indicates that the pacemaker does not respond to sensed electrical signals. Thus, for example, a "VVI" pacemaker delivers pacing stimuli to the ventricle of a patient's heart, senses electrical cardiac activity in the ventricle, and inhibits the delivery of pacing pulses when ventricular signals are sensed. A "DDD" pacemaker, on the other hand, delivers pacing stimuli to both the atrium and ventricle of the patient's heart, senses electrical signals in both the atrium and ventricle, and both triggers and inhibits the delivery of pacing pulses based upon sensed electrical cardiac activity. The delivery of each pacing stimulus by a DDD pacemaker is synchronized with prior sensed or paced events. Other well-known types of pacemakers include AOO, VOO, AAI, VDD, and DVI.

In a conventional DDD pacemaker, two leads are employed—an atrial lead and a ventricular lead. The use of atrial leads, however, may lead to some complications. For example, atrial leads may dislodge a few days after implantation necessitating a return to surgery. As another example, atrial leads may perforate the atrial wall because of the thin nature of atrial wall tissue. Perforation, often called cardiac tamponade, is a serious complication.

SUMMARY

In general, the disclosure is directed to a single-pass pacing lead capable of sensing and pacing both the atria and the ventricles. In some examples, the single-pass pacing lead is connected to a DDD pacemaker. Use of a single-pass pacing lead according to this disclosure may avoid complications associated with use of an atrial lead for DDD pacing. Furthermore, a single-pass pacing lead according to the disclosure may deliver ventricular pacing generally to the left ventricle. Delivery of pacing to the left ventricle, or to the intra-ventricular septum, may provide a more physiologically natural, and thus efficient, cardiac contraction than delivery of pacing to the right ventricle, and particularly the right ventricular apex, as is common with DDD pacemakers having separate atrial and ventricular leads.

In some examples, the single-pass pacing lead comprises four electrodes. In some examples, the lead includes three electrodes configured to be positioned in or near an atrium, e.g., the right atrium, and one electrode configured to be positioned in or near a ventricle, e.g., the left ventricle, when the lead is implanted. In other examples, the lead includes two electrodes configured to be positioned in each of the atrium and ventricle when the lead is implanted. In some examples, one of the electrodes, which is configured to be positioned proximate the coronary sinus ostium when the lead is implanted, comprises a helical element for fixation of the lead to tissue.

In one example, a method comprises introducing into a coronary sinus of a heart a distal portion of a lead body component that comprises a proximal end and a distal end, wherein a first electrode, a second electrode, a third electrode and a fourth electrode are coupled to the lead body component, wherein the first through fourth electrodes are located on the lead body component from most distal to most proximal, wherein introducing the distal portion of the lead body component into the coronary sinus comprises positioning the first electrode in a tributary vein of a great cardiac vein of the heart, the fourth electrode within a right atrium of the heart, and the second or third electrode proximate an ostium of the coronary sinus. The method further comprises attaching the lead body component to a wall of the coronary sinus, proximate the ostium of the coronary sinus, using a fixation member, the fixation member attached to the lead body component proximate to at least one of the second electrode or the third electrode.

In another example, a single-pass cardiac pacing lead is configured to deliver cardiac pacing stimulation to a right atrium and a left ventricle of a heart. The lead comprises a lead body component comprising a proximal end and a distal end. The lead further comprises a first electrode, a second electrode, a third electrode and a fourth electrode coupled to the lead body component, wherein the first through fourth electrodes are located on the lead body component from most distal to most proximal, wherein the first through the fourth electrodes are configured with a relative spacing such that, when a distal portion of the lead body component is implanted within the coronary sinus, the first electrode is positioned within a tributary vein of a great cardiac vein of the heart, the fourth electrode is positioned within the right atrium of the heart, and the second or third electrode is positioned proximate an ostium of the coronary sinus. The lead further comprises a fixation member attached to the lead body component at approximately the second electrode or the third electrode, and spaced along the lead body to be located proximate the ostium of the coronary sinus when the distal portion of the lead body component is implanted within the coronary sinus.

In another example, a system comprises a single-pass cardiac pacing lead configured to deliver cardiac pacing stimulation to a right atrium and a left ventricle of a heart. The lead comprises a lead body component comprising a proximal end and a distal end. The lead further comprises a first electrode, a second electrode, a third electrode and a fourth electrode coupled to the lead body component, wherein the first through fourth electrodes are located on the lead body component from most distal to most proximal, wherein the first through the fourth electrodes are configured with a relative spacing such that, when a distal portion of the lead body component is implanted within the coronary sinus, the first electrode is positioned within a tributary vein of a great cardiac vein of the heart, the fourth electrode is positioned within the right atrium of the heart, and the second or third electrode is positioned proximate an ostium of the coronary sinus. The lead further comprises a fixation member attached to the lead body component at approximately the second electrode or the third electrode, and spaced along the lead body to be located proximate the ostium of the coronary sinus when the distal portion of the lead body component is implanted within the coronary sinus. The system further comprises a processor configured to receive sensed cardiac signals from at least one of the first, second, third or fourth electrodes, and to control electrical stimulation provided by at least one of the first, second, third or fourth electrodes.

The details of one or more examples consistent with the disclosure are set forth in the accompanying drawings and the description below. Other features, objects, and advantages of the disclosure will be apparent from the description and drawings, and from the claims.

DETAILED DESCRIPTION

In general, the disclosure is directed to an IMD system including a single lead that is capable of providing DDD pacing. The lead includes four electrodes, which are spaced in a manner so that when the lead is situated in the patient, at least one of the electrodes is located near the left ventricle, at least one of the electrodes is located near the left atrium, and at least two of the electrodes are located in or near the right atrium. In some examples, the electrode near the left ventricle may be located near the intra-ventricular septum.

The lead is designed to provide pacing and sensing of both the atria and the ventricles without requiring the introduction of a lead or an electrode into the right ventricle. The lead may be referred to as a single-pass, left-sided, DDD lead. The lead may be referred to as a single-pass in that the single lead places electrodes proximate to both an atrium and a ventricle. The lead may be referred to as left-sided in that the lead places electrodes proximate to the left ventricle, e.g., via the coronary sinus, rather than the right ventricle. It has been suggested that pacing the right ventricle, particularly near the apex of the heart, may provide less than ideal contraction of the ventricles. Additionally, by avoiding the right ventricle for pacing and sensing, a second lead may be introduced to the right ventricle to provide a defibrillation stimulus (e.g., "shock") as needed. The defibrillation lead may desirably have a smaller diameter and greater flexibility than a lead that includes conductors for pacing and sensing electrodes in addition to those for defibrillation.

In addition, the disclosure is directed to a lead that includes a helix fixation member that is located proximal of the lead tip. In some examples, the helix fixation member may be located at or near the electrode located proximate the left atrium. In some examples, the helix fixation member may be located at or near one of the electrodes located proximate the right atrium. In some examples, the helix fixation member may be located at or near an electrode located proximate the ostium of the coronary sinus. The use of the helix fixation member at one of the electrodes located in the atrium allows for active fixation the atrium and delivery of pacing pulses to the atrium. In some examples, the helix fixation member is used to affix the lead to the luminal wall of the coronary vein or the great cardiac vein.

Figure 1:
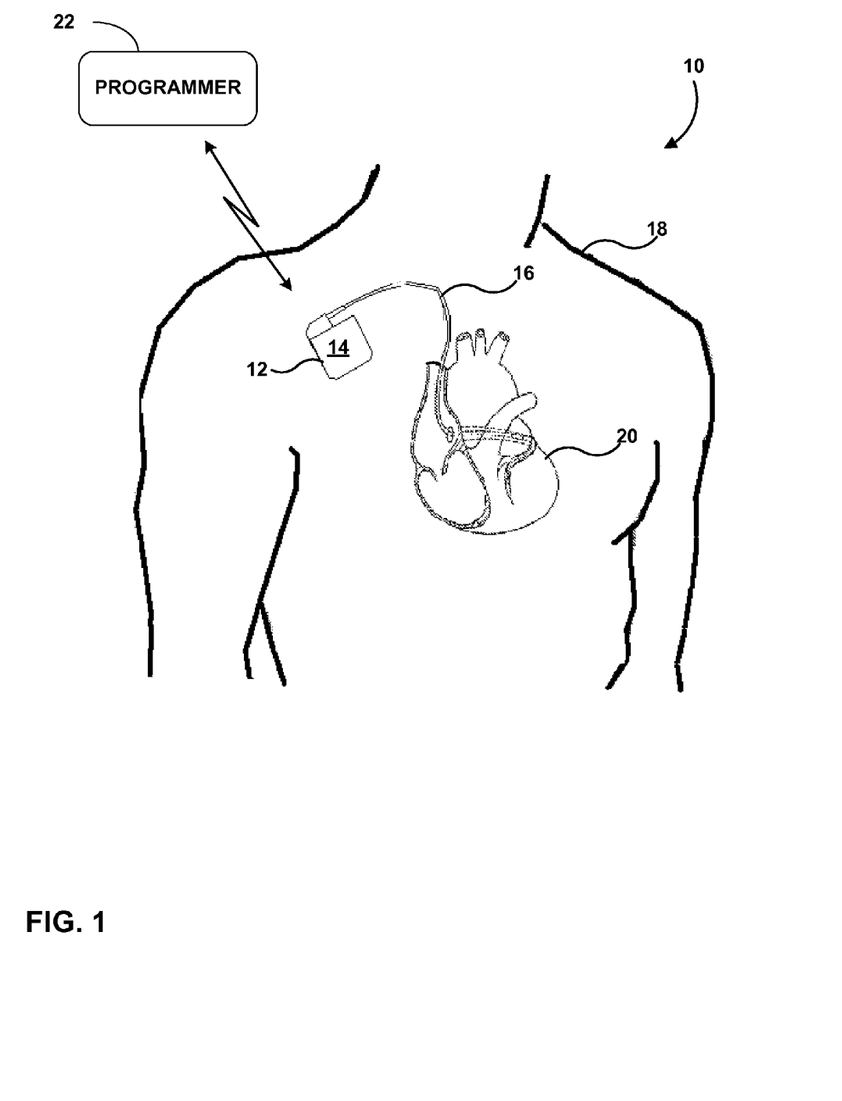
FIG. 1 is a conceptual diagram illustrating an example implantable medical device system comprising an implantable medical device (IMD) and an implantable medical lead coupled to the IMD.

FIG. 1 is a conceptual diagram illustrating an example implantable medical device system 10 comprising an IMD 12, and implantable medical lead 16 electrically coupled to IMD 12. In the example shown in FIG. 1, system 10 is implanted within a patient 18 to deliver electrical stimulation therapy to the heart 20 of patient 18. Patient 18 ordinarily, but not necessarily, will be a human patient.

In the example shown in FIG. 1, IMD 12 is a cardiac pacemaker, cardioverter, defibrillator, or pacemaker-cardioverter-defibrillator (PCD) that generates therapeutic electrical stimulation for pacing, cardioversion or defibrillation, which may take the form of pulses, e.g., about 1 to about 5 volt pacing pulses at a rate of about 50 to about 150 pulses per minute, or infrequent cardioversion/defibrillation stimuli of about 100 to about 800 volts. Lead 16 includes four electrodes that are each positioned within (e.g., intravascularly) heart 20 in order to deliver the therapeutic electrical stimulation from IMD 12 to heart 20.

In the illustrated example, a distal end of lead 16 is positioned proximate to the left ventricle (LV) of patient 18, and more particularly, within the coronary sinus or a coronary vein accessed via the coronary sinus. In the illustrated example, lead 16 is configured for intravenous introduction into heart 20. For example, lead 16 may have a lead body diameter between about 1 and about 3 millimeter. When lead 16 is positioned within the coronary sinus or coronary vein, the four electrodes (not shown in FIG. 1) may be positioned so that the two most proximal electrodes are in or near the right atrium (RA) close to the AV node. In some examples, one electrode may be in the RA and one electrode may be within the coronary sinus. The third electrode may be located in the great cardiac vein and the fourth, and most distal, electrode may be located in one of the tributaries of the great coronary vein. For example, the fourth electrode may be located in the lateral coronary vein, the anterior coronary vein, or the anterior—lateral coronary vein. As described in further detail below, this configuration of electrodes allows for atrial sensing and pacing as well as ventricular sensing and pacing, as needed, using a single lead. Housing 14 of IMD 12 may be used as an anode in some examples.

To facilitate passage down narrow vessels, the electrodes of lead 16 are nearly the same diameter as the lead body, usually a fraction of a millimeter thicker to make sure they contact the vessel wall. Likewise, the helix fixation member 32 (FIG. 2) may also be slightly, e.g., a fraction of a millimeter, thicker than the lead body. Electrodes are typically about 0.2 to about 0.5 cm long. The whole lead is about 50 to about 100 cm in length, depending on the size of the patient.

As shown in FIG. 1, system 10 may also include a programmer 22, which may be a handheld device, portable computer, or workstation that provides a user interface to a clinician or other user. The clinician may interact with the user interface to program stimulation and sensing parameters for IMD 12, which may include, as examples, the electrodes of lead 16 which are activated for providing stimulation versus sensing, as well as selection from among different pacing modes, rate-response modes, inter-chamber intervals, arrhythmia detection algorithms, arrhythmia termination therapy progressions.

Programmer 22 supports telemetry (e.g., radio frequency telemetry) with IMD 12 to download stimulation parameters and, optionally, upload operational or physiological data stored by IMD 12. In this manner, the clinician may periodically interrogate IMD 12 to evaluate efficacy and, if necessary modify the operational parameters of the IMD. IMD 12 and programmer 22 may communicate via wireless communication as shown in FIG. 1. Programmer 22 may, for example, communicate via wireless communication with IMD 12 using RF telemetry techniques known in the art.

In some examples, at least one of the electrodes of lead 16 may function as a sensor that senses a physiological parameter of patient 12, such as, but not limited to, electrogram (EGM) parameters, a heart rate, QRS width, or atrioventricular (AV) dissociation. Sense electrodes may be the same electrodes used for delivery of electrical stimulation to patient 18, or different electrodes.

Figure 2:
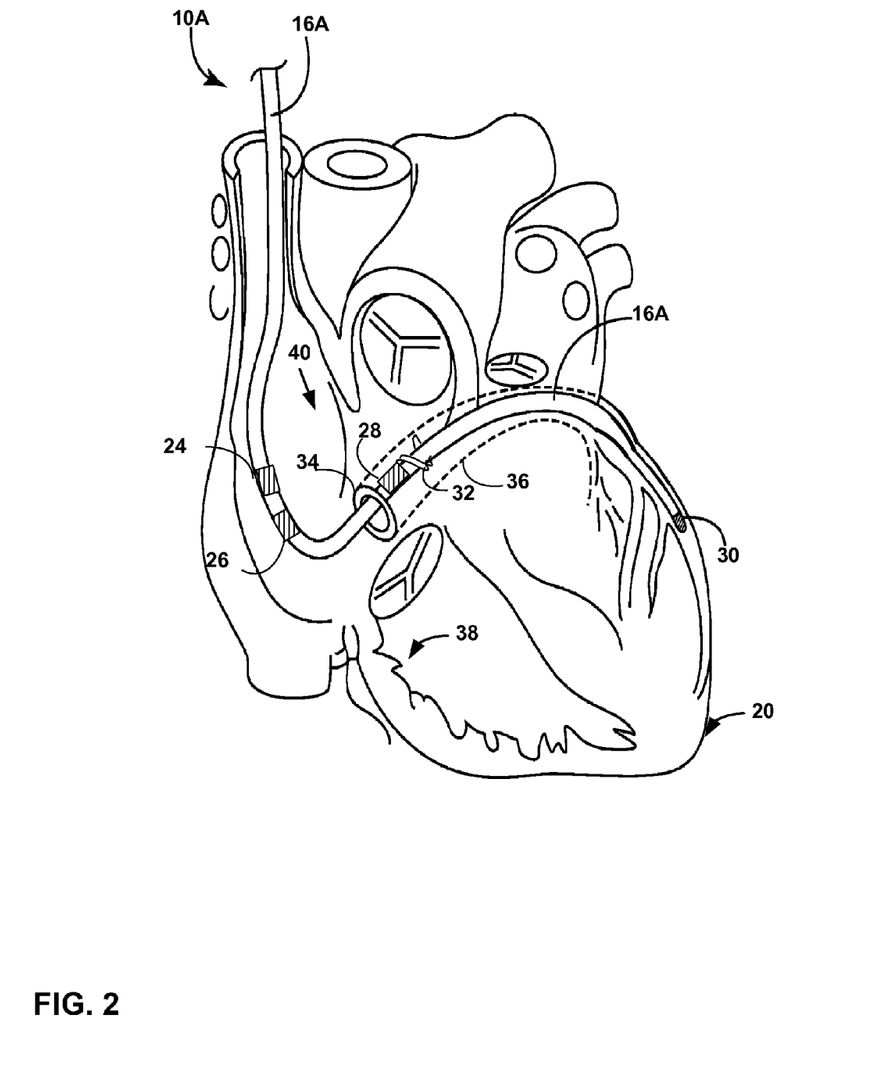
FIG. 2 is a conceptual diagram illustrating an example configuration of the lead of the system of FIG. 1 in a patient's heart in greater detail.

FIG. 2 is a conceptual diagram illustrating an example configuration of the lead 16A of system 10A of FIG. 1 within heart 20. Lead 16A of system 10A includes electrodes 24, 26, 28 and 30. Lead 16A also includes a helix fixation member 32. In some examples, helix fixation member 32 is also electrode 28, e.g., helix fixation member 32 is conductive and acts as, or as part of, electrode 28. Lead 16A may be anchored to the wall of the coronary sinus 36, near ostium 34 via helix fixation member 32. Lead 16A may be anchored by turning the lead clockwise to embed the helix fixation member 32 into the wall of the coronary sinus 36 when the electrodes are situated as desired within the heart.

As shown in FIG. 2, the electrodes of lead 16 are spaced so that electrodes 24 and 26 are located in RA 40. In some examples, electrodes 24 and 26 are floating electrodes within RA 40, e.g., do not necessarily contact the tissue of RA 40. For example, electrodes 24 and 26 may be floating atrial sense electrodes that function in a manner similar to floating sense electrodes in a conventional VDD lead. In some examples, electrodes 24 and 26 are located near the heart septum. In the example of FIG. 2, electrode 28 is located within coronary sinus 36. Electrode 30 is located at the distal end of lead 16, within one of the tributary veins of the great coronary vein. For example, electrode 30 may be located in the lateral coronary vein, the anterior coronary vein, or the anterior-lateral coronary vein. The tributary vein is selected so that electrode 30 is roughly adjacent the left ventricle (LV) and not as near the right ventricle (RV) apex. Electrodes 24 and 26 may be located less than approximately 1 cm apart. In some examples, electrodes 24 and 26 may be less than approximately 0.5 cm apart. The close spacing of atrial electrodes 24 and 26 may help to avoid R-wave over sensing, including far-field R-wave oversensing. In addition, the location of electrodes may aide in detecting the occurrence of an A-V block. In some examples, either of electrodes 24 and 26 may used in a unipolar configuration with an electrode formed on or by housing 14 to sense atrial activity. In some examples, electrode 28 may serve as an atrial pace cathode, with the housing 14 of IMD 12 functioning as the atrial pace anode.

Electrode 28 may also serve as the ventricular sense-anode while electrode 30 may serves as the ventricular sense-cathode. The housing 14 may also function as an anode when electrode 30 delivers stimulation to LV 40.

Figure 3:
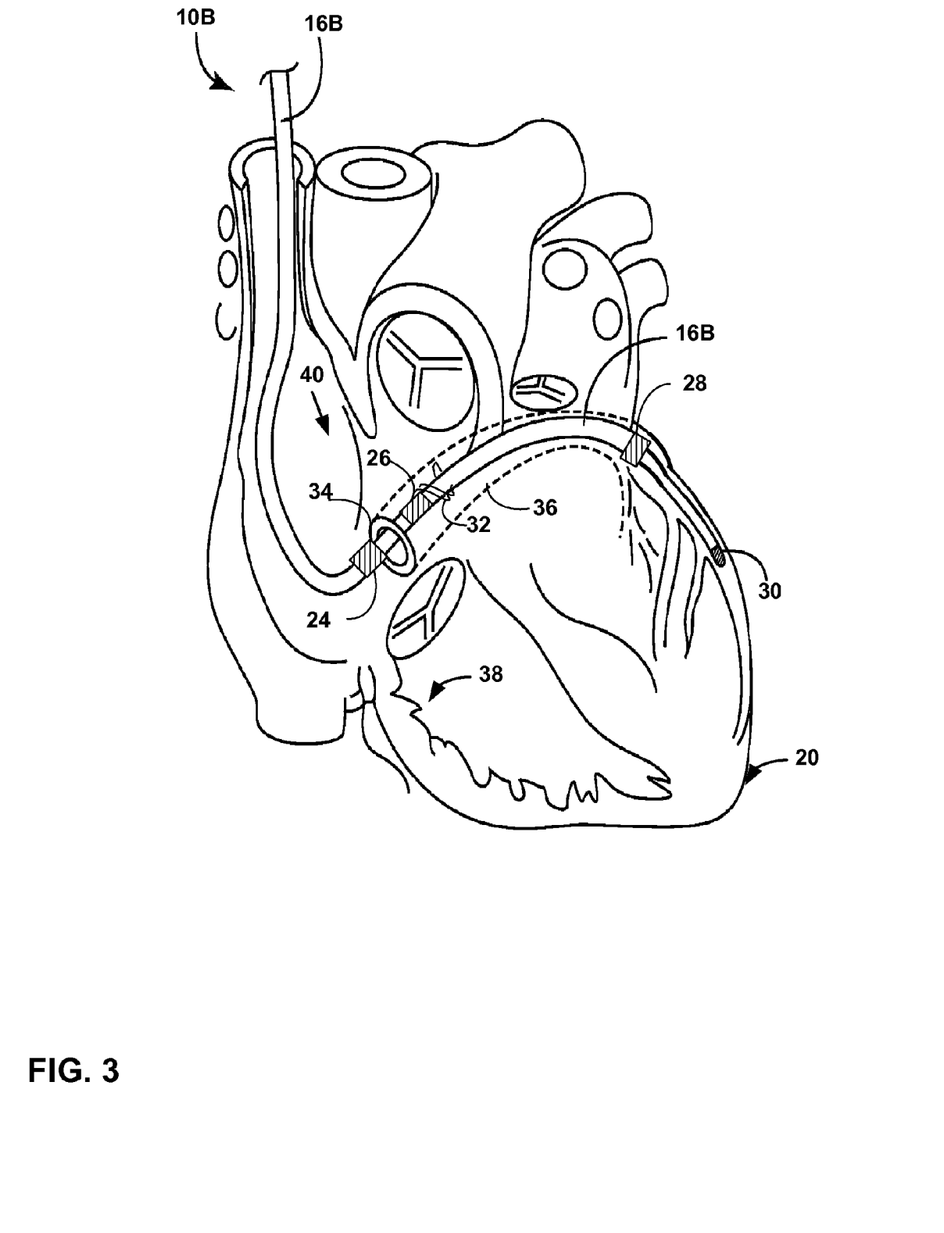
FIG. 3 is a conceptual diagram illustrating another example configuration of the lead of the system of FIG. 1 in a patient's heart in greater detail.

FIG. 3 is a conceptual diagram illustrating another example configuration of a lead 16B of a system 10B within heart 20. Lead 16B of system 10B includes electrodes 24, 26, 28 and 30. Lead 16B also includes a helix fixation member 32, which may act as or be electrically coupled to electrode 26. Lead 16B may be anchored to the wall of the coronary sinus 36, near ostium 34 via helix fixation member 32. Lead 16B may be anchored by turning the lead clockwise to embed the helix fixation member 32 into the wall of the coronary sinus 36 when the electrodes are situated as desired within the heart. As shown in FIG. 3, the electrodes of lead 16 are spaced so that electrode 24 is located within RA 40. Electrode 26 is located proximate to coronary sinus ostium 34. Electrode 28 is located in the great cardiac vein, near the left atrium. Electrode 30 is located at the distal end of lead 16, within one of the tributary veins of the great coronary vein. For example, electrode 30 may be located in the lateral coronary vein, the anterior coronary vein, or the anterior-lateral coronary vein. The tributary vein is selected so that electrode 30 is roughly adjacent the left ventricle (LV) and not as near the right ventricle (RV) apex.

Electrodes 24 and 26 may act as a bipolar pair to sense atrial activity. Electrodes 24 and 26 may be located less than approximately 1 cm apart. In some examples, electrodes 24 and 26 may be less than approximately 0.5 cm apart. The close spacing of atrial electrodes 24 and 26 may help to avoid R-wave over sensing, including far-field R-wave oversensing. In addition, the location of electrodes may aide in detecting the occurrence of an A-V block. In some examples, either of electrodes 24 and 26 may used in a unipolar configuration with an electrode formed on or by housing 14 to sense atrial activity.

In some examples, electrode 26 may serve as an atrial pace cathode, with the housing 14 of IMD 12 functioning as the atrial pace anode. Electrode 28 may serve as the ventricular sense-anode while electrode 30 may serves as the ventricular sense-cathode, or either of electrodes 28 and 30 may be used in a unipolar configurations to sense electrical activity of the ventricles. Furthermore, electrodes 28 and 30 may be used to deliver bipolar pacing or other stimulation to LV 40, or either or both of electrodes 28 and 30 may be used in a unipolar configuration with an electrode of housing 14 to deliver unipolar stimulation. In The housing 14 may function as an anode when electrodes 28 or 30 stimulate. In some examples, both of electrodes 28 and 30 may be used in a unipolar configuration to deliver sequential pacing to the ventricles. For example, electrode 28 may provide a first pacing pulse. A delay of approximately 10 milliseconds may be programmed between the pacing pulse from electrode 28 and a second pacing pulse from electrode 30. During delay electrode 30 is in sensing mode. If electrode 30 senses that the pulse from electrode 28 was capture, then the pacing pulse from electrode 30 is inhibited. However, if the pacing pulse from electrode 28 does not result in captures, then electrode 30 provides the second pacing pulse.

Figure 4A:
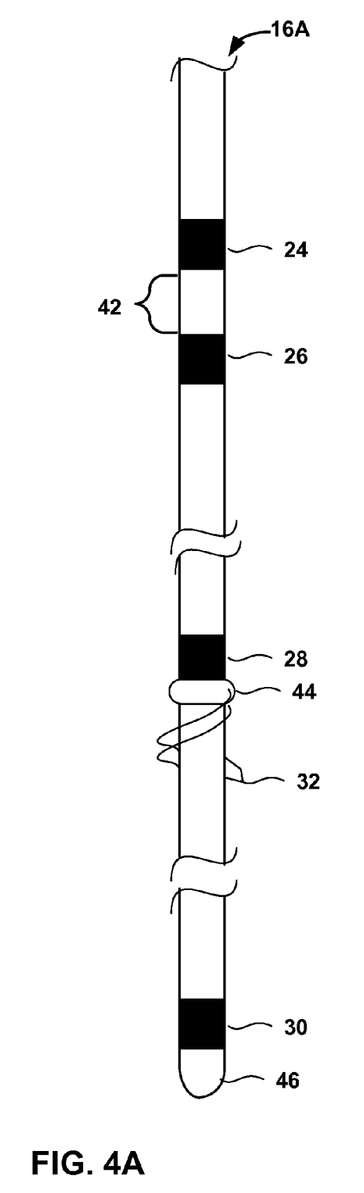
FIG. 4A illustrates an example lead consistent with the present disclosure.

FIG. 4A shows an example lead 16A. Lead 16A includes electrodes 24, 26, 28 and 30. In the example lead of FIG. 4A, fixation member 32 is located near electrode 28.

As shown in FIG. 4A, lead 16A may include a stopper 44. Stopper 44 may prevent or substantially prevent tissue from wedging between the lead body and fixation member 32. Wedged tissue may make it difficult to re-position the lead, or to remove the lead, e.g., due to conductor breakage or infection. During fixation of lead 16A, the lead may be turned until the myocardium contacts stopper 44.

In some examples, helix fixation member 32 may be unconnected electrically from the adjacent electrode or coated in a polymer or other nonconductive material to mask the wire. In some examples, a polymer may be used to control the surface area of the combination of the electrode 28 and the fixation member 32. In some examples, where the fixation member acts as an electrode, it may be helpful to limit surface area in order to keep pacing thresholds low.

In some examples of FIG. 4A, the spacing 42 between electrodes 24 and 26 may be between approximately 0.3 cm and approximately 1.0 cm. In some examples, the spacing 42 is measured from the center points of electrodes 24 and 26. In instances where the spacing is too large, the atrial sense electrodes may sense the R-waves and P-wave at approximately the same time. In some examples, once lead 16 is in place within heart 20, electrodes 24 and 26 may be approximately on the atrial septum. In some examples electrodes 24 and 26 are located near the AV node. In some examples of FIG. 4A, the spacing between electrodes 26 and 28 is between approximately 3 cm to approximately 5 cm, and the spacing between electrodes 28 and 30 is between approximately 10 cm to approximately 15 cm.

Figure 4B:
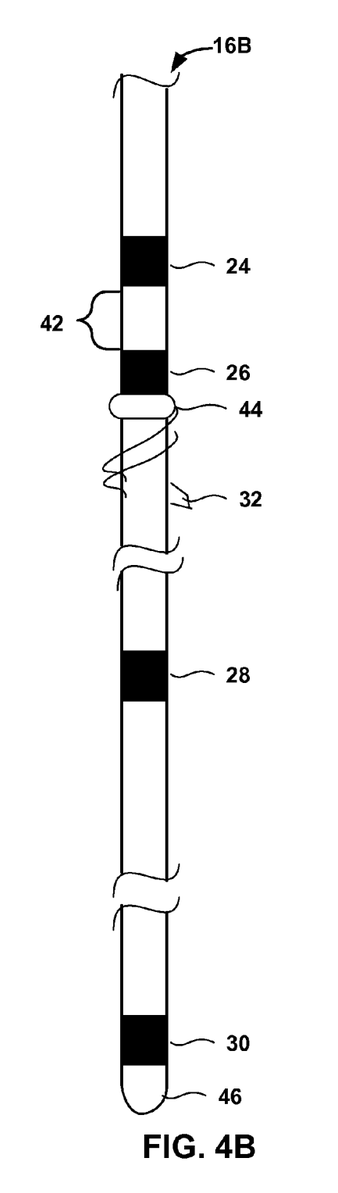
FIG. 4B illustrates another example lead consistent with the present disclosure.

FIG. 4B shows an example configuration of lead 16B. Lead 16B includes electrodes 24, 26, 28 and 30. In the example lead of FIG. 4B, fixation member 32 is located near electrode 28, but may otherwise be substantially similar to fixation member 32 described above with respect to FIG. 4A. As shown in FIG. 4B, lead 16B may include a stopper 44, which may be substantially similar to and provide substantially similar functionality to the stopper 44 described above with respect to lead 16A and FIG. 4A.

In some examples, the spacing 42 between electrodes 24 and 26 may be between approximately 0.3 cm and approximately 1.0 cm. In some examples, the spacing 42 is measured from the center points of electrodes 24 and 26. In instances where the spacing is too large, the atrial sense electrodes may sense the R-waves and P-wave at approximately the same time. In some examples, electrodes 24 and 26 are located near the AV node. In some examples, the spacing between electrodes 26 and 28 is between approximately 10 cm to approximately 15 cm, and the spacing between electrodes 28 and 30 is between approximately 1 cm and approximately 2 cm.

As shown in FIGS. 4A and 4B, in some examples, electrode 30 may be close to, but not directly at the tip 46. The tip 46 may be made of polyurethane or another polymer base. In some examples, lead 16 may include a flourovisible or radioopaque tip. The use of a flourovisible tip may allow for tracking of lead 16 during implantation. In such examples, the flourovisible tip may be used to track the advancement of a lead 16 through the coronary sinus, the great coronary vein, and one a selected tributary vein. The tributary vein may be selected in order to locate electrode 30 adjacent the LV and less near the RV apex. The tributary vein may be the lateral coronary vein, the anterior coronary vein, the anterior-lateral coronary vein or the posterior-lateral vein, as examples. In some examples, lead 16 may taper towards the tip 46 in order to more easily navigate the tributary veins.

In some examples, pacing lead 16 may have a hollow center for guidewire or stylet delivery. Guidewires are soft and flexible while stylets are relatively stiff. During implantation of pacing lead 16 a guidewire may first be passed into the desired vessel tributary and the lead 16 passed over the guidewire. In addition, the stylet may also be used to help the helix fixation member engage with the myocardium. This may be done by pre-bending the stylet wire. In some examples, the implanter may interchange stylets and guidewires; a guidewire to coax the tip into a tributary and a stylet to nudge the helix up against the vessel wall. In other examples, a steerable catheter may be used to deliver pacing lead 16 and also used to nudge the helix close to the vessel wall so the helix engages the tissue of the vessel. In some examples, the electrode or the base of the helix fixation point may have a window cut into the metal. The window may appear white via fluoroscopy, and opaque during rotation, thereby allow the physician to confirm that the rotation at the proximal end of the lead is actually turning the helix fixation member 32.

Figure 5:
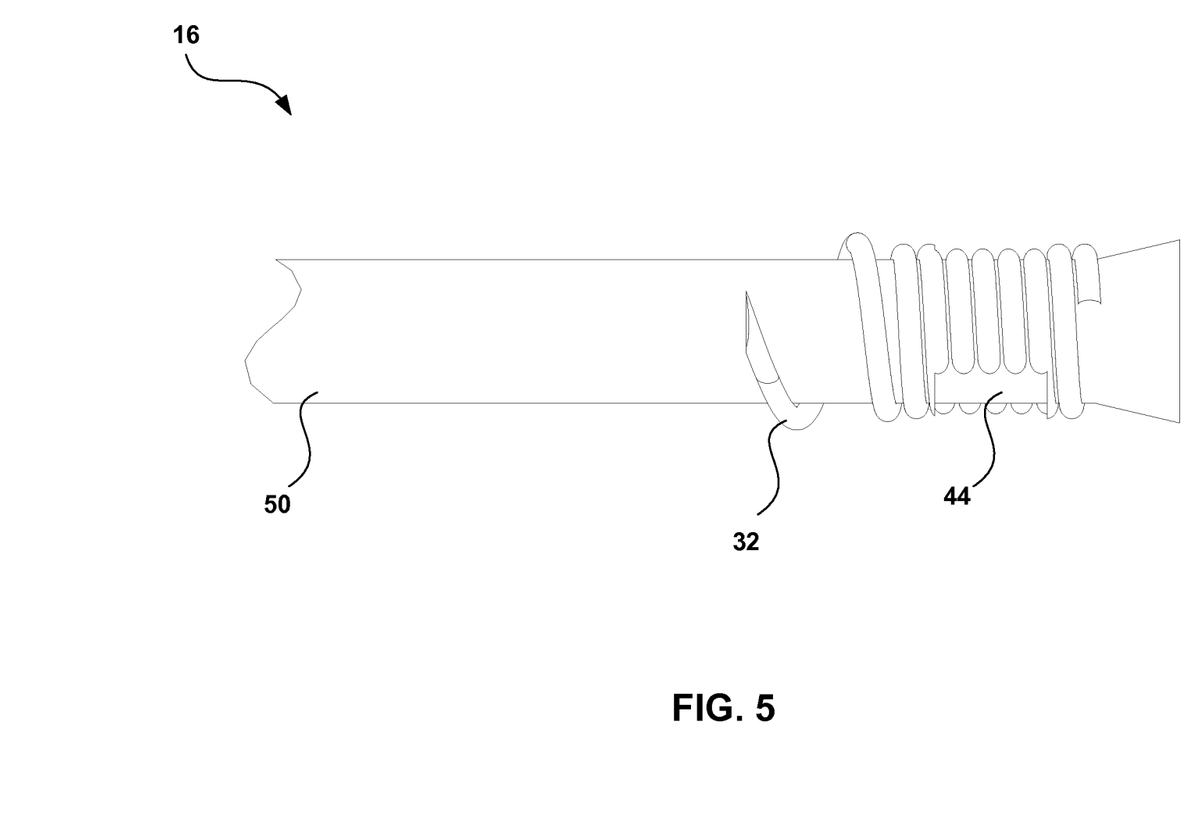
FIG. 5 is a conceptual diagram illustrating a fixation member of a lead consistent with the present disclosure.

FIG. 5 is a conceptual diagram further illustrating a fixation member 32 of a lead 16 consistent with the present disclosure. More particularly, FIG. 5 illustrates an example in which fixation member 32 comprises a helix that is formed on or attached to the lead body 50 of lead 16, and encircles the lead body a plurality of times. Lead 16 may be anchored by turning lead body 50 clockwise about its longitudinal axis to embed the helix fixation member 32 into the wall of the coronary sinus 36 (FIGS. 2 and 3) when the electrodes are situated as desired within the heart.

Fixation member 32 may be a ¾ turn helix made of approximately 0.1 to approximately 0.2 mm thick wire, which may be round or flat stock. Example materials that may be used for the wire of fixation member 32 include platinum, platinum-alloy, or stainless steel. Another example, material that may be used for the wire of fixation member 32 because of its pacing characteristics is titanium, which may be either bare or coated with titanium oxide.

FIG. 5 also further illustrates stopper 44. Stopper 44 may prevent or substantially prevent tissue from wedging between the lead body and fixation member 32. Wedged tissue may make it difficult to re-position the lead, or to remove the lead, e.g., due to conductor breakage or infection. During fixation of lead 16, the lead may be turned until the myocardium contacts stopper 44.

Stopper 44 may comprise a material, which may be insulative. Stopper 44 may be formed on one portion of the circumference of fixation member 32, e.g., may be absent from other portions of the circumference of fixation member 32. Stopper 44 may be formed, as shown in FIG. 5, along a portion of the length of the fixation member as it encircles the lead body, but may be absent from a sufficient portion of the fixation member to allow the fixation member to penetrate the myocardium.

Figure 6:
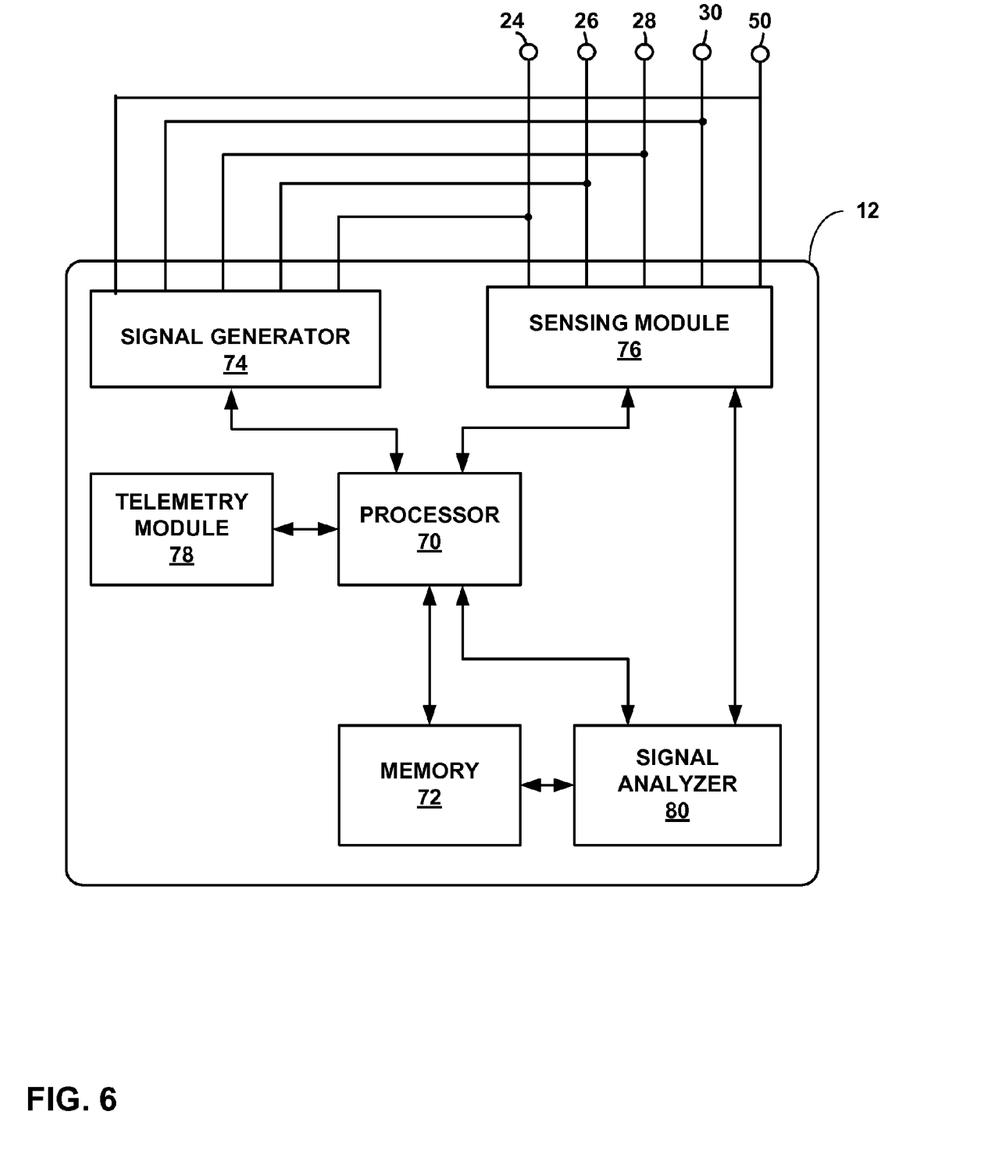
FIG. 6 is a block diagram illustrating an IMD consistent with the present disclosure

FIG. 6 is a block diagram illustrating an IMD 12 consistent with the present disclosure. In the illustrated example, IMD 12 include a processor 70, memory 72, signal generator 74, sensing module 76, telemetry module 78, and signal analyzer 80. Memory 72 includes computer-readable instructions that, when executed by processor 70, cause IMD 12 and processor 70 to perform various functions attributed to IMD 12 and processor 70 herein. Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof. Generally, processor 70 controls signal generator 74 and sensing module 76 to sense cardiac activity and deliver stimulation therapy to heart 20 of patient 18 according to a selected one or more operational modes, programs or parameters, which may be stored in memory 72.

Signal generator 74 is configured to generate and deliver electrical stimulation therapy to patient 18. As shown in FIG. 6, signal generator 74 is electrically coupled to electrodes 24, 26, 28 and 30 of lead 16. Signal generator 74 is also connected to a housing electrode 50 on or integral with housing 14. For example, signal generator 74 may deliver pacing pulses, to heart 20 via at least two of electrodes 24, 26, 28, 30 and 50. In other examples, signal generator 74 delivers stimulation in the form of signals other than pulses such as sine waves, square waves, or other substantially continuous time signals.

Signal generator 74 may include a switch module (not shown) and processor 70 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes. Electrical sensing module 76 monitors electrical cardiac signals from any combination of electrodes 24, 26, 28, 30 and 50. Sensing module 76 may also include a switch module which processor 70 controls to select which of the available electrodes are used to sense the heart activity, depending upon which electrode combination is used in the current sensing configuration.

Sensing module 76 may include one or more detection channels, each of which may comprise an amplifier. The detection channels may be used to sense the cardiac signals. Some detection channels may detect events, such as R-waves or P-waves, and provide indications of the occurrences of such events to processor 70 and/or signal analyzer 80. One or more other detection channels may provide the signals to an analog-to-digital converter, for conversion into a digital signal for processing or analysis by processor 70 or signal analyzer 80.

For example, sensing module 76 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 70 then uses that detection in measuring frequencies of the sensed events.

In one example, at least one narrow band channel may include an R-wave or P-wave amplifier. In some examples, the R-wave and P-wave amplifiers may take the form of an automatic gain controlled amplifier that provides an adjustable sensing threshold as a function of the measured R-wave or P-wave amplitude. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

In some examples, sensing module 76 includes a wide band channel which may comprise an amplifier with a relatively wider pass band than the narrow band channels. Signals from the electrodes that are selected for coupling to the wide-band amplifier may be converted to multi-bit digital signals by an analog-to-digital converter (ADC) provided by, for example, sensing module 76, processor 70, or signal analyzer 80. Processor 70 may analyze the digitized version of signals from the wide band channel. Processor 70 may employ digital signal analysis techniques to characterize the digitized signals from the wide band channel to, for example, detect and classify the patient's heart rhythms. In other examples, the signal analyzer 80 employs digital signal analysis techniques to characterize the digitized signals from the wide band channel.

Processor 70 may detect and classify the patient's heart rhythm based on the cardiac electrical signals sensed by sensing module 76 employing any of the numerous signal processing methodologies known in the art. In other examples, sensing module 76 provides the cardiac electrical signals sensed directed to signal analyzer 80. In some examples, sensing module 76 provides the sensed cardiac electrical signals to both processor 70 and signal analyzer 80 for different signal processing. In various examples, processor 70 may maintain escape interval counters that may reset upon sensing of R-waves by sensing modules 76. The value of the count present in the escape interval counters when reset by sensed depolarizations may be used by processor 70 to measure the durations of R-R intervals, which are measurement that may be stored in memory 72 and may be used by cardiac signal analyzer 80. Processor 70 may use the count in the interval counters to detect a tachyarrhythmia, such as ventricular fibrillation or ventricular tachycardia. A portion of memory 72 may be configured as a plurality of recirculating buffers, capable of holding a series of measured intervals, which may be analyzed by processor 70 to determine whether the patient's heart 20 is presently exhibiting atrial or ventricular tachyarrhythmia.

Figure 7:
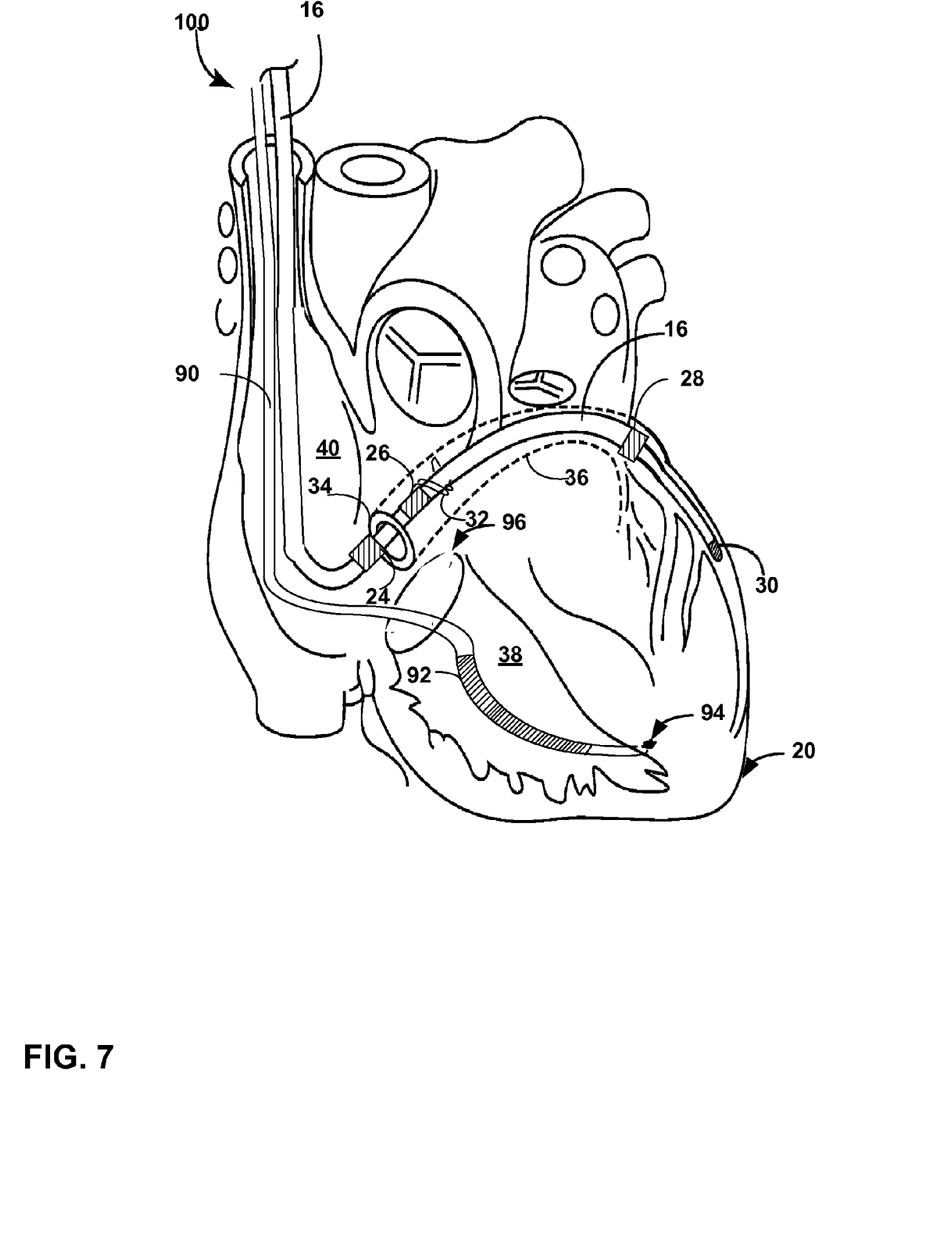
FIG. 7 is a conceptual diagram illustrating an example configuration of a system including a pacing lead and a defibrillation lead.

In some examples, IMD 12 is also connected to a defibrillation lead with a coil electrode as shown in FIG. 7, and discussed below. Processor 70 may control signal generator 74 to provide a defibrillation stimulus (e.g., "shock") to heart 20 via the coil electrode in response to a determination that heart 20 is exhibiting tachyarrhythmia that does not respond to anti-tachycardia pacing pulses from the electrodes of pacing lead 16.

FIG. 7 is a conceptual diagram illustrating an example configuration of a system 100, including a pacing lead 16 and a defibrillation lead 90, consistent with the present disclosure. Lead 16 of system 10 may be configured consistent with lead 16A or 16B as described above. The location of pacing lead 16 leaves RV 38 free from a lead or a portion of a lead. This allows for, in examples such as the one shown in FIG. 6, lead 90 to be introduced into RV 38. Lead 90 may include a high voltage coil electrode 92 and a fixation member 94. In some examples, lead 90 does not include a sensing ring or pacing tip distal to the coil. This allows the coil of lead 90 to be placed deeper into the apex of RV 38 than a defibrillation lead that also includes sensing capabilities. Lead 90 does not need to include a sensing electrode because sensing may be achieved using the electrodes 24, 26, 28 and 30 of lead 16.

In some examples, a single wire defibrillation lead 90 may be used as an auxiliary shocking coil. For example, electrode 92 may part of an azygos shocking vector. In some examples, electrode 92 is a 3.6F defibrillation coil. In some examples, lead 90 may be implanted at a different time then lead 16. For example, when a patient's condition changes so that an implantable cardioverter-defibrillator (ICD) is needed instead of simply a pacemaker, lead 90 can be added without need to remove or replace lead 16. In some examples, lead 90 may be implanted at the same time as lead 16 in anticipation of the patient's transition from needing simply a pacemaker to needing an ICD. This may result in a less invasive surgery, or no surgery, at the time of conversion from pacemaker to ICD. For example, the only incision may be to replace IMD 12, shown in FIG. 1, with an IMD that can control both lead 16 and lead 90. In some examples, IMD 12 may simply be reprogrammed to start detecting cardiac signals indicative of the need of a defibrillation shock, and to provide stimulation via electrode 92 of lead 90.

In some examples, the use of lead 90 and lead 16 may take up less space within heart 20 and less space within the vessels then a combined therapy lead. The combination of lead 90 and a MRI-safe lead 16 may also result in a MRI-safe defibrillator system when mated with a MRI-safe IMD. In addition, in some examples, system 100 provides less susceptibility to flex failures and insulation breach failures than other ICD systems.

Figure 8:
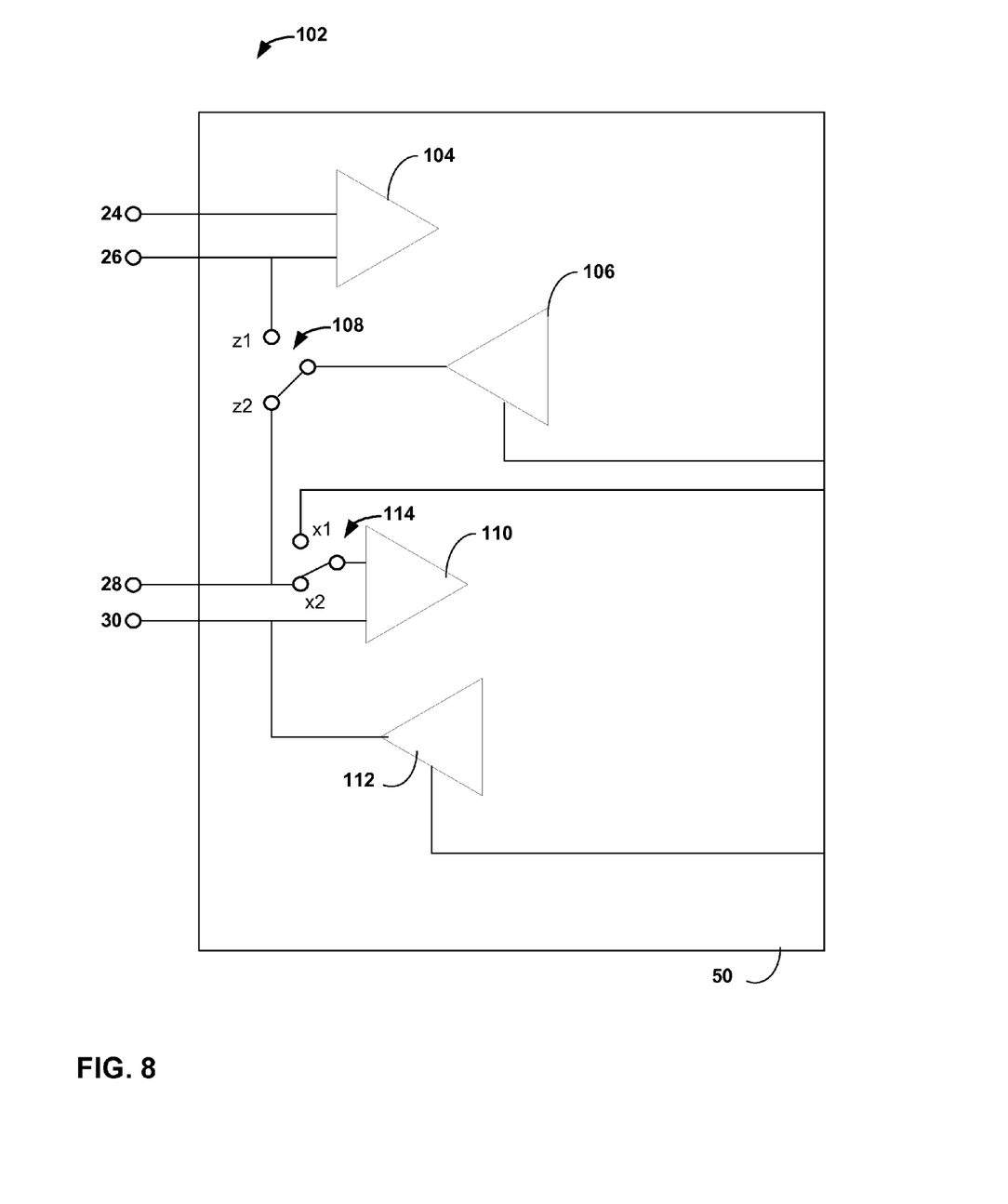
FIG. 8 is a block diagram illustrating a pacing and sensing circuit consistent with the present disclosure.

FIG. 8 is a block diagram illustrating how, through inclusion of switches 108 and 114, an IMD may provide DDD pacing and sensing via a single-pass lead, such as lead 16A of FIG. 4A or lead 16B of FIG. 4B, or a standard 2-lead system. Stimulating and sensing circuit 102 includes an atrial sensing circuit 104, an atrial stimulating circuit 106, a ventricular sensing circuit 110, a ventricular stimulating circuit 112 and switches 108 and 114. In some examples, atrial sensing circuit 104 and ventricular sensing circuit 110 are part of sensing module 76 as shown in FIG. 5 and atrial pacing circuit 106 and ventricular pacing circuit 112 are part of signal generator 74 as shown in FIG. 6. In these examples, atrial sensing is achieved using bipolar sensing with electrodes 24 and 26. The use of the two closely spaced electrodes 24 and 26 allows for sensing of atrial activity without the signal being overpowered by the larger ventricular signal. Atrial signals are one-third the strength of ventricular signals so closely spaced bipolar atrial electrodes are important for the accurate function of single-pass leads, such as lead 16A of FIG. 4A or lead 16B of FIG. 4B.

Atrial stimulation may occur via either electrode 28, in examples coupled to lead 16A of FIG. 4A, or electrode 26, in examples coupled to lead 16B of FIG. 4B. As shown, with switches 108 and 114 programmed in the Z2,X2 position, and lead 16A of FIG. 4A coupled to the IMD, atrial sensing is accomplished across electrode pair 24/26 and atrial stimulation is delivered from electrode 28 (as the cathode) to the IMD housing 50 as the anode (that is, unipolar atrial stimulation). In such examples, ventricular sensing would be bipolar with electrode 28 as the anode, and stimulation would be unipolar with housing 50 as the anode. Electrode 30 would act as the cathode for both ventricular sensing and stimulation.

With switch 108 programmed to the Z1 position, and either lead 16B of FIG. 4B or a standard 2-lead system plugged into the IMD, the IMD may provide bipolar atrial sensing and unipolar atrial stimulation, as well as unipolar ventricular stimulation. Further, in such as configuration, a choice of bipolar ventricular sensing (switch 114 in the X1 position), or unipolar ventricular sensing (switch 114 in X2 position) may be provided. Accordingly, by the inclusion of these switches in an IMD, the IMD may accommodate single-pass leads, such as lead 16A of FIG. 4A or lead 16B of FIG. 4B, or a standard 2-lead arrangement. Generally, unipolar stimulation with housing 50 as the anode is not disadvantageous. In fact, a unipolar stimulation configuration with housing electrode 50 for stimulus return may conserve the energy of an IMD power source relative to a bipolar stimulation configuration.

As shown in FIG. 8, cardiac signal propagation across the ventricle is sensed using bipolar or unipolar sensing, depending on the programming of switch 114. Ventricular sensing circuit 110 is connected to electrodes 28 and 30 when switch 114 is in the X2 position. In this configuration electrode 28 is the sense anode. When switch 114 is in the X1 position, ventricular sensing circuit 110 uses housing electrode 50 as the sense anode. Because the cardiac signal in the ventricle is more robust than in the atrium, unipolar sensing is generally not a problem. In either configuration, electrode 30 is programmed as the sense cathode. Ventricular stimulation occurs at electrode 30. Ventricular stimulation circuit 112 uses a unipolar stimulation configuration with electrode 30 and housing electrode 50.

Figure 9:
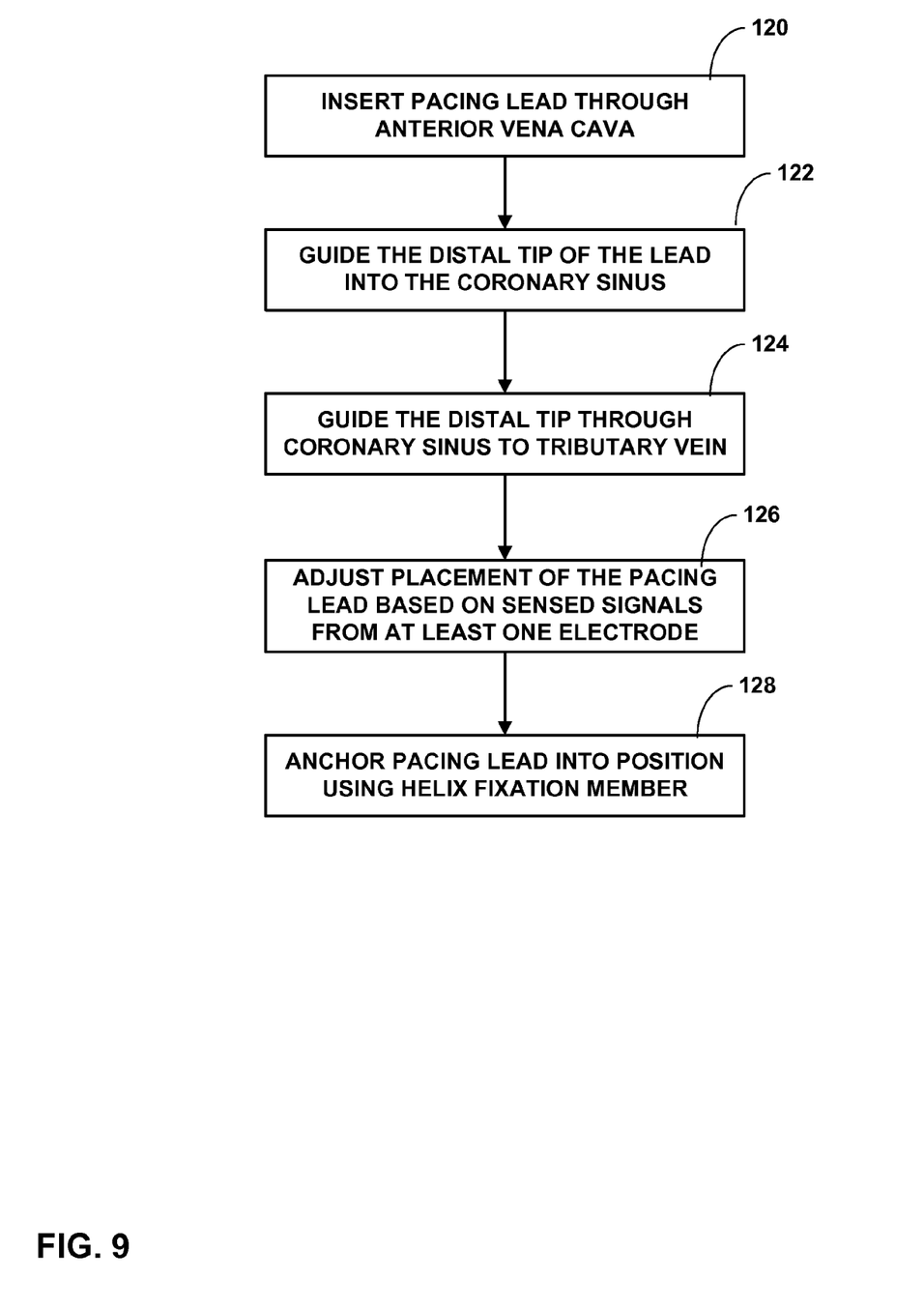
FIG. 9 is a flow diagram illustrating an example method of implanting a single-pass left-sided DDD pacing lead consistent with the present disclosure.

FIG. 9 is a flow diagram illustrating a method of implanting a single pacing lead 16 consistent with the present disclosure. When implanting pacing lead 16, a physician inserts pacing lead 16 through the anterior vena cava (120) into the right atrium 40 of heart 20. In some examples, pacing lead 16 is introduced into the vascular system at the clavicle. In some examples, pacing lead 16 may include a flourovisible tip to aid the physician in navigating the vascular system and patient heart 20. In some examples, a catheter or guide wire or stylet may be used to aid in guiding pacing lead 16 through the anterior vena cava into heart 20. In some examples, a physician may inject a contrast agent in order to aid in visualization of the pathway for the pacing lead 16.

The physician continues to guide the distal tip of pacing lead 16 into coronary sinus 36 (122). The physician then guides the distal tip through the coronary sinus 36 to a selected tributary vein (124). In some examples, the physician guides the distal tip of pacing lead 16 through the coronary sinus to the great cardiac vein, and down a preselected tributary vein. The tributary vein may be the lateral coronary vein, the anterior coronary vein, the anterior-lateral coronary vein, or the posterior-lateral vein. In some examples the tributary vein is selected so that the distal tip, and electrode 30, is roughly in the left ventricular and not in the right ventricle apex. In some examples, electrode 30 may be located hear the septum of heart 20.

After the tip has been introduced into the tributary vein, the physician can adjust the placement of pacing lead 16 based on sensed signals from at least one electrode on pacing lead 16 (126). Signals may be collected while electrodes 24 and 26 are in a number of positions based on the movement of pacing lead 16 within heart 20 to achieve desired signal capture. In some examples, the signals collected while moving pacing lead 16 may be used to map the progression of the atrial signal across heart 20. In some examples, both electrodes 24 and 26 of lead 16 are used to detect cardiac signals and determine an appropriate final location of lead 16. Electrodes 24 and 26 may be floating electrodes within the right atrium. In some examples, movement of pacing lead 16 used to obtain an atrial signal detected by electrodes 24 and 26 of a desired signal quality. In some examples, the final placement of pacing lead 16 may result in electrodes 24 and 26 being located in the right atrium, near the ostium of the coronary sinus. In some examples, electrode 26 may be inside of the ostium of the coronary sinus.

After the appropriate placement of pacing lead 16 has been determined based on sensed cardiac signals, the physician anchors pacing lead 16 in the final position using helix fixation member 32 (128). In some examples, the physician turns the lead in a clockwise manner to embed the helix in the wall of the vein in which the helix fixation member is located. In some examples, the helix fixation member may be in the coronary sinus and in other examples the helix fixation member may be in the great cardiac vein. In some examples, the guide wire may be used to press the helix fixation member against the wall of the vein by bowing the guidewire. In some examples, a stylet may be used to bend pacing lead 16 and push the pacing lead near helix fixation member 32 towards the wall of the vein.

Various examples have been described. These and other examples are within the scope of the following claims.

The invention claimed is:

1. A method comprising:
introducing into a coronary sinus of a heart a distal portion of a lead body component that comprises a proximal end and a distal end, wherein a first electrode, a second electrode, a third electrode and a fourth electrode are coupled to the lead body component, wherein the first through fourth electrodes are located on the lead body component from most distal to most proximal, wherein introducing the distal portion of the lead body component into the coronary sinus comprises positioning the first electrode in a tributary vein of a great cardiac vein of the heart, the fourth electrode within a right atrium of the heart, and the second or third electrode proximate an ostium of the coronary sinus; and
attaching the lead body component to a wall of the coronary sinus, proximate the ostium of the coronary sinus, using a fixation member, the fixation member attached to the lead body component proximate to at least one of the second electrode or the third electrode;
wherein the fixation member is configured to penetrate myocardial tissue.

2. The method of claim 1, wherein the fixation member comprises a helix that encircles the lead body component, the method further comprising rotating the lead body in order to engage the fixation member with the wall of the coronary sinus.

3. A method comprising:
introducing into a coronary sinus of a heart a distal portion of a lead body component that comprises a proximal end and a distal end, wherein a first electrode, a second electrode, a third electrode and a fourth electrode are coupled to the lead body component, wherein the first through fourth electrodes are located on the lead body component from most distal to most proximal, wherein introducing the distal portion of the lead body component into the coronary sinus comprises positioning the first electrode in a tributary vein of a great cardiac vein of the heart, the fourth electrode within a right atrium of the heart, and the second or third electrode proximate an ostium of the coronary sinus; and
attaching the lead body component to a wall of the coronary sinus, proximate the ostium of the coronary sinus, using a fixation member, the fixation member attached to the lead body component proximate to at least one of the second electrode or the third electrode;
wherein the fixation member comprises a helix that encircles the lead body component, the method further comprising rotating the lead body in order to engage the fixation member with the wall of the coronary sinus; and
wherein the lead body component is rotated until a stopper on the lead body proximate the helix fixation member engages the wall of the coronary sinus.

4. The method of claim 1, further comprising introducing a second lead body comprising a high voltage coil electrode into a right ventricle of the heart.

5. The method of claim 1, wherein the fixation member is proximate to the second electrode, and wherein the third electrode is located in the right atrium when the distal portion of the lead body component is positioned within the coronary sinus.

6. The method of claim 5, further comprising applying atrial pacing via the second electrode.

7. The method of claim 5, wherein the fixation member is the second electrode.

8. The method of claim 1, wherein the fixation member is proximate to the third electrode, and wherein the second electrode is located in a great cardiac vein when the distal portion of the lead body component is positioned within the coronary sinus.

9. The method of claim 8, further comprising delivering atrial pacing via the third electrode.

10. The method of claim 8, wherein the fixation member is the third electrode.

11. The method of claim 1, further comprising delivering ventricular pacing via at least one of the first and second electrodes.

12. The method of claim 1, further comprising delivering sequential ventricular pacing pulses via the second and first electrodes.

13. A single-pass cardiac pacing lead configured to deliver cardiac pacing stimulation to a right atrium and a left ventricle of a heart, the lead comprising:
a lead body component comprising a proximal end and a distal end;
a first electrode, a second electrode, a third electrode and a fourth electrode coupled to the lead body component, wherein the first through fourth electrodes are located on the lead body component from most distal to most proximal, wherein the first through the fourth electrodes are configured with a relative spacing such that, when a distal portion of the lead body component is implanted within the coronary sinus, the first electrode is positioned within a tributary vein of a great cardiac vein of the heart, the fourth electrode is positioned within the right atrium of the heart, and the second or third electrode is positioned proximate an ostium of the coronary sinus; and
a fixation member attached to the lead body component at approximately the second electrode or the third electrode, and spaced along the lead body to be located proximate the ostium of the coronary sinus when the distal portion of the lead body component is implanted within the coronary sinus;
wherein the fixation member is configured to penetrate myocardial tissue.

14. The lead of claim 13, wherein the fixation member comprises a helix that encircles the lead body component, and is configured to penetrate myocardial tissue when the lead is rotated.

15. The lead of claim 14, further comprising a stopper located on the lead body component proximate the helix fixation member.

16. The lead of claim 13, wherein the fixation member is located proximate to the second electrode, and the third electrode is spaced along the lead body to be located in the right atrium when the distal portion of the lead body component is positioned within the coronary sinus.

17. The lead of claim 16, wherein the second electrode is configured to apply atrial pacing.

18. The lead of claim 16, wherein the helix fixation member is the second electrode.

19. The lead of claim 13, wherein the helix fixation member is located proximate to the third electrode, and wherein the second electrode is spaced along the lead body to be located in the great cardiac vein when the distal portion of the lead body component is positioned within the coronary sinus.

20. The lead of claim 19, wherein the third electrode is configured to provide atrial pacing.

21. The lead of claim 19, wherein the helix fixation member is the third electrode.

22. A system comprising:
a single-pass cardiac pacing lead configured to deliver cardiac pacing stimulation to a right atrium and a left ventricle of a heart, the lead comprising:
a lead body component comprising a proximal end and a distal end,
a first electrode, a second electrode, a third electrode and a fourth electrode coupled to the lead body component, wherein the first through fourth electrodes are located on the lead body component from most distal to most proximal, wherein the first through the fourth electrodes are configured with a relative spacing such that, when a distal portion of the lead body component is implanted within the coronary sinus, the first electrode is positioned within a tributary vein of a great cardiac vein of the heart, the fourth electrode is positioned within the right atrium of the heart, and the second or third electrode is positioned proximate an ostium of the coronary sinus, and
a fixation member attached to the lead body component at approximately the second electrode or the third electrode, and spaced along the lead body to be located proximate the ostium of the coronary sinus when the distal portion of the lead body component is implanted within the coronary sinus; and
a processor configured to receive sensed cardiac signals from at least one of the first, second, third or fourth electrodes, and to control electrical stimulation provided by at least one of the first, second, third or fourth electrodes;
wherein the processor is further configured to detect an AV block based on signals sensed by the third and fourth electrodes and, in response to detecting the AV block, provide a ventricular pace electrical stimulation pulse via the first electrode.

23. The system of claim 22, further comprising a defibrillation lead configured to deliver a defibrillation electrical shock emanating from the right ventricle of the heart.

24. The system of claim 22, wherein the processor is further configured to provide sequential ventricular pacing pulses via the second and first electrodes.

* * * * *